US008986228B2

(12) United States Patent
Auchinleck et al.

(10) Patent No.: US 8,986,228 B2
(45) Date of Patent: Mar. 24, 2015

(54) METHOD AND APPARATUS FOR MONITORING SURGICAL TRACTION

(75) Inventors: Geoffrey Auchinleck, Vancouver (CA);
Stephen Lewis Leckenby, Victoria (CA); Kyle Cameron, Victoria (CA); Gregory Vincent Browne, Victoria (CA)

(73) Assignee: Trimanus Medical, Inc., Vancouver, BC (CA)

( * ) Notice: Subject to any disclaimer, the term of this patent is extended or adjusted under 35 U.S.C. 154(b) by 636 days.

(21) Appl. No.: 13/235,608

(22) Filed: Sep. 19, 2011

(65) Prior Publication Data
US 2013/0072822 A1    Mar. 21, 2013

(51) Int. Cl.
*A61B 5/103* (2006.01)
*A61B 5/117* (2006.01)
*A61B 17/66* (2006.01)
*A61B 5/00* (2006.01)

(52) U.S. Cl.
CPC .............. *A61B 5/1036* (2013.01); *A61B 17/66* (2013.01); *A61B 5/4848* (2013.01); *A61B 2562/0261* (2013.01)
USPC ................... 600/587; 128/882; 5/624; 5/648; 600/592; 600/595; 602/32; 602/33; 602/36

(58) Field of Classification Search
CPC ........... A61G 13/0036; A61G 13/1245; A61G 2203/32; A61B 5/4504; A61B 5/4538; A61H 1/0222; A61H 1/0266
USPC ............... 128/882; 5/624, 648; 600/587, 592, 600/595; 602/32, 33, 36
See application file for complete search history.

(56) References Cited

U.S. PATENT DOCUMENTS

| | | | | |
|---|---|---|---|---|
| 1,238,224 | A * | 8/1917 | Vickers | 602/23 |
| 2,053,753 | A * | 9/1936 | Wellington | 248/231.61 |
| 2,875,753 | A * | 3/1959 | Sulmonetti | 602/34 |
| 2,909,175 | A * | 10/1959 | Kinnear | 602/33 |
| 3,756,227 | A * | 9/1973 | Sager | 602/23 |
| 4,608,971 | A * | 9/1986 | Borschneck | 602/23 |
| 4,641,637 | A * | 2/1987 | Rosen | 602/35 |
| 4,807,618 | A * | 2/1989 | Auchinleck et al. | 128/878 |
| 4,817,592 | A * | 4/1989 | Auchinleck et al. | 128/855 |
| 4,913,163 | A * | 4/1990 | Roger et al. | 600/595 |
| 5,027,799 | A * | 7/1991 | Laico et al. | 602/20 |
| 5,094,249 | A * | 3/1992 | Marras et al. | 600/594 |
| 5,104,103 | A * | 4/1992 | Auchinleck et al. | 269/74 |
| 5,162,039 | A * | 11/1992 | Dahners | 602/23 |
| 5,511,571 | A * | 4/1996 | Adrezin et al. | 135/66 |
| 5,608,934 | A * | 3/1997 | Torrie et al. | 5/624 |
| 5,658,315 | A * | 8/1997 | Lamb et al. | 606/241 |
| 5,669,908 | A * | 9/1997 | Gracilla | 606/53 |
| 5,704,356 | A * | 1/1998 | Shmueli | 600/407 |
| 6,286,164 | B1 * | 9/2001 | Lamb et al. | 5/600 |
| 6,634,043 | B2 * | 10/2003 | Lamb et al. | 5/600 |
| 6,872,187 | B1 * | 3/2005 | Stark et al. | 602/16 |
| 6,962,220 | B2 * | 11/2005 | Takenaka et al. | 180/8.6 |
| 7,022,094 | B2 * | 4/2006 | Buckman et al. | 602/23 |
| 7,246,390 | B2 * | 7/2007 | Mitsuishi et al. | 5/648 |
| 7,507,216 | B2 * | 3/2009 | Buckman et al. | 602/32 |

(Continued)

*Primary Examiner* — Sean Dougherty
(74) *Attorney, Agent, or Firm* — Hancock Hughey LLP

(57) ABSTRACT

Apparatus is described for measuring and displaying the magnitude of traction forces applied to a patient's lower limbs during surgery, and for measuring the direction and magnitude of counter-traction forces applied to the patient's body by the perineal post located at the patient's groin to oppose traction forces applied to the patient's lower limbs.

12 Claims, 6 Drawing Sheets

(56) References Cited

U.S. PATENT DOCUMENTS

| | | | |
|---|---|---|---|
| 7,753,862 B2 * | 7/2010 | Branch et al. | 601/5 |
| 7,762,975 B2 * | 7/2010 | Memminger | 602/39 |
| 7,878,992 B2 * | 2/2011 | Mitsuishi et al. | 601/23 |
| 7,935,069 B2 * | 5/2011 | Buckman et al. | 602/39 |
| 7,947,006 B2 * | 5/2011 | Torrie et al. | 602/32 |
| 8,171,570 B2 * | 5/2012 | Adarraga | 2/22 |
| 8,177,733 B2 * | 5/2012 | Ashihara et al. | 601/35 |
| 8,211,046 B2 * | 7/2012 | Buckman et al. | 602/39 |
| 8,303,524 B2 * | 11/2012 | Ikeuchi | 601/34 |
| 8,753,294 B2 * | 6/2014 | Branch et al. | 600/592 |
| 2002/0023298 A1 * | 2/2002 | Lamb et al. | 5/600 |
| 2004/0133983 A1 * | 7/2004 | Newkirk et al. | 5/624 |
| 2007/0055193 A1 * | 3/2007 | Daury | 602/33 |
| 2007/0251011 A1 * | 11/2007 | Matta et al. | 5/624 |
| 2008/0214976 A1 * | 9/2008 | Memminger | 602/39 |
| 2011/0190676 A1 * | 8/2011 | Torrie et al. | 602/32 |
| 2011/0213285 A1 * | 9/2011 | Buckman et al. | 602/36 |

\* cited by examiner

METHOD AND APPARATUS FOR MONITORING SURGICAL TRACTION

FIELD OF THE INVENTION

The present invention relates generally to the medical field, and more particularly to apparatus and method for monitoring the traction force applied to limbs during orthopaedic surgery, where traction is applied between a patient's foot or leg and a restraining post located at the patient's groin. The invention teaches monitoring and displaying both the force applied to the patient's legs and the magnitude and direction of the force applied to the patient's groin in order to limit the risk of injury to the patient.

BACKGROUND OF THE INVENTION

In the treatment of certain medical conditions it is desirable to provide a traction force to a patient's limb or limbs. Examples include distraction of the hip for hip arthroscopy or distraction of fractures of the leg bones in order to re-align the broken bones to ensure correct healing ('fracture reduction'). In each of these cases, tension is applied to the patient's lower limb or foot. In order to maintain the traction force, it is necessary to apply a counter-force to prevent the patient's body being pulled off the operating table.

Various means have been developed to apply this counter-traction force, including harnesses and patient positions that use the patient's weight as the counter-force, however the most common approach is to provide a cylindrical post (called a 'perineal post') located at the patient's groin. In this position, traction force is usually applied to both the operative and non-operative limb to prevent the patient's pelvis rotating about the perineal post.

Examples of such apparatus are described in U.S. Pat. No. 1,697,121 (Knebel), U.S. Pat. No. 2,658,507 (Neufeld) and numerous others, generally called 'fracture tables'. Variations of fracture tables provide means to apply and adjust traction forces using screw mechanisms or suspended weights (see U.S. Pat. No. 4,802,464 (Deprez) and U.S. Pat. No. 3,088,460 (Wright)).

Although this technique for applying limb traction has been in use for more than 100 years, it still presents a risk of significant injury to the patient. Anatomical structures in the groin in both the male and female are delicate and can suffer grievous injury if the perineal post applied force directly along the midline. In males, damage to the perineal nerve can cause loss of sensation in the penis, whereas in the female, damage to the labia can result.

For this reason, the perineal post is generally well padded and located off-centre in the patient's groin to avoid direct application of the traction force to the mid-line of the patient's groin. Various types of perineal posts are known in the art, all generally intended to distribute the force on the perineum over a large area to minimize the pressure applied to the patient's tissue.

A common failing of all fracture tables and perineal posts know in the art is that there is no means to measure and display the force being applied to the perineum, nor the direction of the force, during surgery. Distal traction devices such as screws or weights can easily be (and sometimes are) equipped with indicating scales to show the amount of traction force applied. Unfortunately, such indicating scales are usually not visible during surgery as they are under the surgical drapes or otherwise obscured, and do not indicate the magnitude or direction of the force applied to the patient's groin. Furthermore, during the course of surgery, it may be necessary to alter the direction or magnitude of the traction force applied to the patient's limb in order to provide visualization of or access to the surgical site. When such changes in the direction and magnitude of the traction force are made, these indicating scales do not provide adequate feedback to the surgeon.

In summary, current fracture tables depend on traction applied through the lower limb, countered by a perineal post. In the surgical setting, there is no indication of the traction force applied to the operative or non-operative limb visible to the surgeon, nor is there any indication of the counter-traction force applied by the perineal post or the direction of the force applied to the patient's groin.

The object of the current invention is to provide means for measuring and displaying to a surgeon the traction force applied to the patient's operative and non-operative limbs, to measure and display the counter-traction force applied to the patient's perineum by the perineal post, and to provide an indication as to the direction of application of the force to the patient's perineum by the perineal post. This will ensure that the surgeon is aware if the traction force as applied from time to time during surgery is exceeding acceptable limits, or if the direction of the force applied to the patient's perineum by the perineal post poses a risk to the fragile structures of the patient's groin.

BRIEF DESCRIPTION OF THE DRAWINGS

The features and advantages of the present invention will become apparent upon reference to the following detailed description of the preferred embodiments and to the drawings, wherein.

DETAILED DESCRIPTION OF THE PREFERRED EMBODIMENTS

Figure 1:
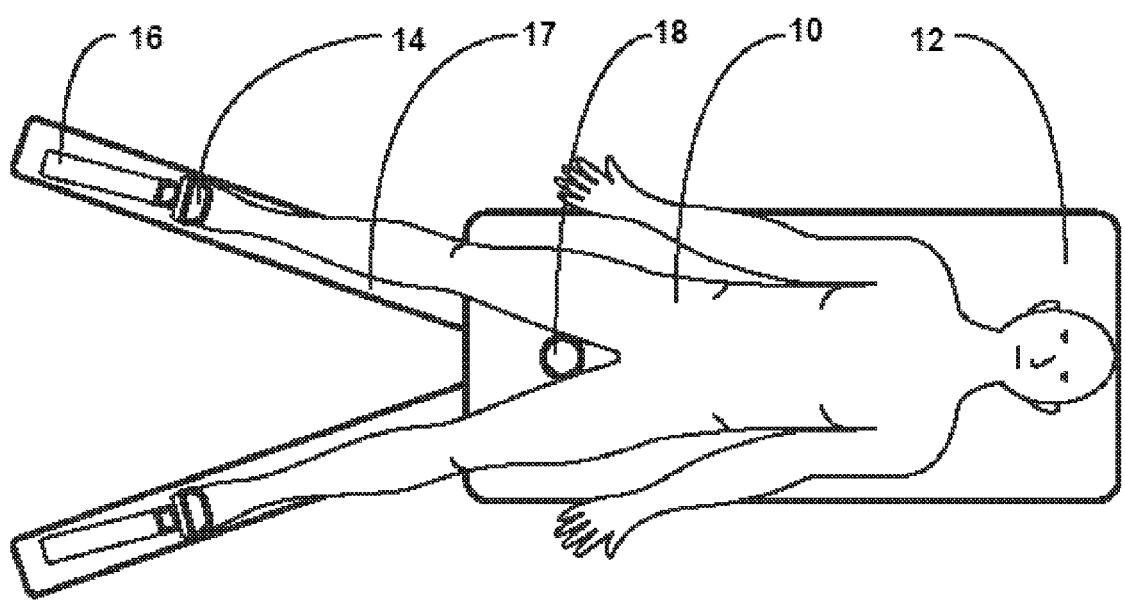
FIG. 1 is an illustration of a typical position for a patient on a fracture table.

With reference now to the drawings, FIG. 1 illustrates a typical position for a patient undergoing surgery that requires traction to the lower extremity. Patient 10 is positioned on operating table 12 in the supine position. The patient's feet are put into patient applied parts 14, which in this embodiment are boot-like devices which provide a means to apply tension to the lower limb along the axis of the limb by pulling on the feet. These patient applied parts are connected to traction application devices 16, which in this embodiment are screw-thread devices which are disposed to move patient applied parts 14 towards or away from the patient's body in order to increase or decrease the traction force applied to the lower limbs.

Traction application devices 16 are connected to support arms 17 which are in turn connected to the body of operating table 12 so that turning the screw thread of traction application device 16 will apply a force generally along the axis of the patient's leg with respect to operating table 12.

To prevent patient 10 from being pulled along the surface of operating table 12 upon application of the traction force, perineal post 18 is mounted to operating table 12 and is located in the patient's groin. Perineal post 18 provides a counter force to the force applied to the patient's legs by traction application devices 16, thereby preventing the movement of patient 10's body in the direction of the applied traction force. In this way, significantly large tension forces can be created in the lower limbs of patient 10.

It should be noted that traction can be applied to patient 10's lower limbs in other orientations using a substantially similar apparatus. For example, patient 10 could be positioned in a prone position, or in a lateral position while allowing and traction to be applied to the lower limbs in a similar manner. Further, although the current embodiment uses a boot-like apparatus to apply traction force through the feet, it is known in the art to insert a pin crosswise through the bones of the lower limb and connect this pin to traction application devices 16 to apply traction force directly to the bones of patient 10. Such variations in technique do not substantially change the function or intent of the present invention.

Returning now to the configuration of FIG. 1, perineal post 18 is usually positioned to one side or the other of the mid-line of patient 10's body. This ensures that the force applied by perineal post 18 is not applied directly to patient 10's groin, which has the potential to cause injury. Further, when applying traction force with traction application devices 16, more traction may be applied to one of patient 10's legs than the other in order to rotate patient 10's pelvis and direct the force applied by perineal post 18 away from patient 10's mid line.

Figure 2:
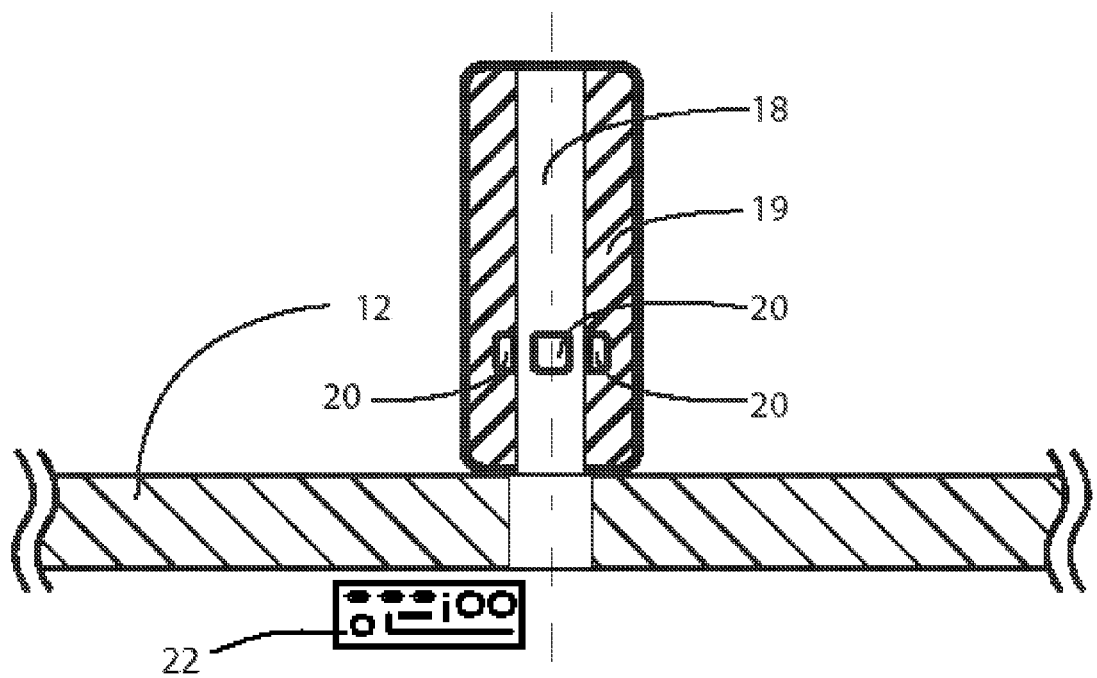
FIG. 2 depicts a perineal post in accordance with the invention.

FIG. 2 is a side view of perineal post 18. In the current invention, perineal post 18 is equipped with four strain gages 20, attached to perineal post 18 as two sets of opposing pairs, each located 90 degrees apart and covered with padding 19. This arrangement of strain gages 20 permits measuring the amount of strain experienced by the perineal post along two generally perpendicular axes, each pair of strain gages 20 providing opposing strain sensing to maximize sensitivity. The perpendicular axes ensure that forces applied to perineal post 18 by the body of patient 10 can be resolved into a vector in the plane of operating table 12.

Common conductive foil type strain gages are used in the preferred embodiment. These strain gages consist of a conductive foil pattern on a flexible backing, which is glued to perineal post 18 using cyanoacrylate adhesive. When a bending moment is applied to perineal post 18, this causes a very slight deformation of perineal post 18, which in turn causes deformation of strain gages 20. This deformation results in a very slight change in the electrical resistance of the conductive foil pattern, which is proportional to the deformation and hence the bending moment applied to perineal post 18. The signals generated by strain gages 20 are thus proportional to the bending moments applied to the post.

Strain gages 20 are connected to amplifying and transmitting circuitry 22 which serves to amplify the signals generated by strain gages 20, convert the resulting analog signals to digital signals and transmit these signals over a wireless connection.

As is known in the art, such an arrangement of strain gages can be calibrated by adjusting the gain of the amplifier stage of circuitry 22 so that a known force applied to perineal post 18 results in a specific output level. In this way, the output signal can be correlated with the force applied to perineal post 18.

Figure 3:
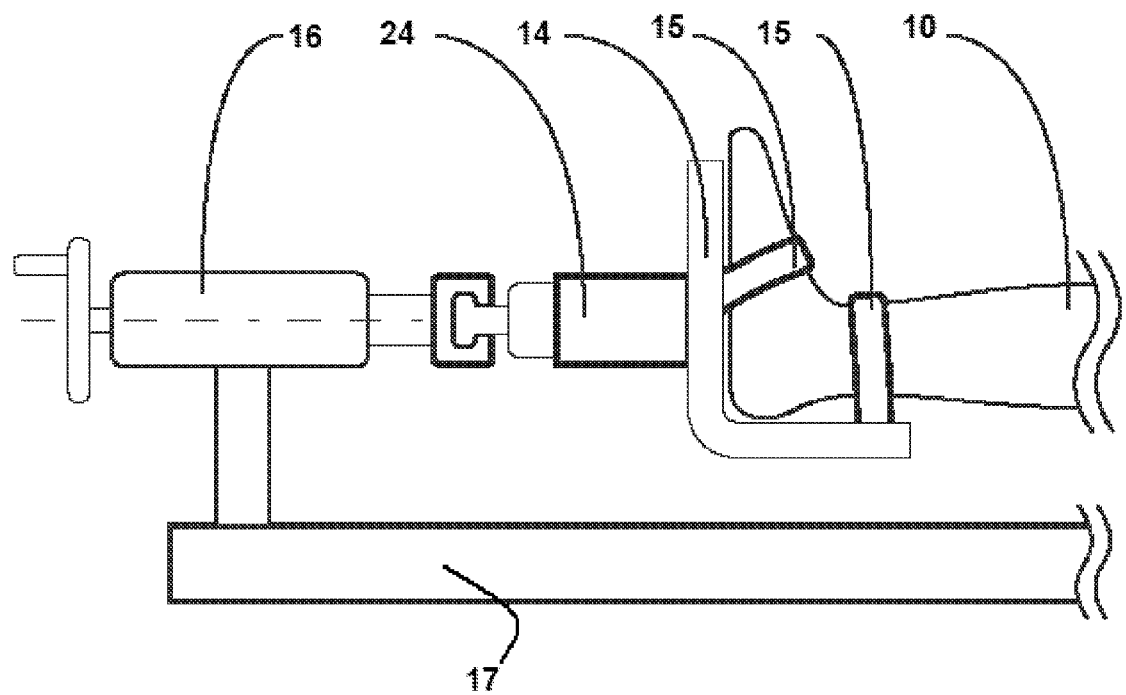
FIG. 3 illustrates a typical mechanism for applying traction force to a patient's foot.

FIG. 3 is a lateral view of one of traction application devices 16 connected to patient applied part 14 which in turn is connected to the foot of patient 10 with straps 15. Connected between patient applied part 14 and traction application device 16 is load cell 24, hereinafter described.

Figure 4:
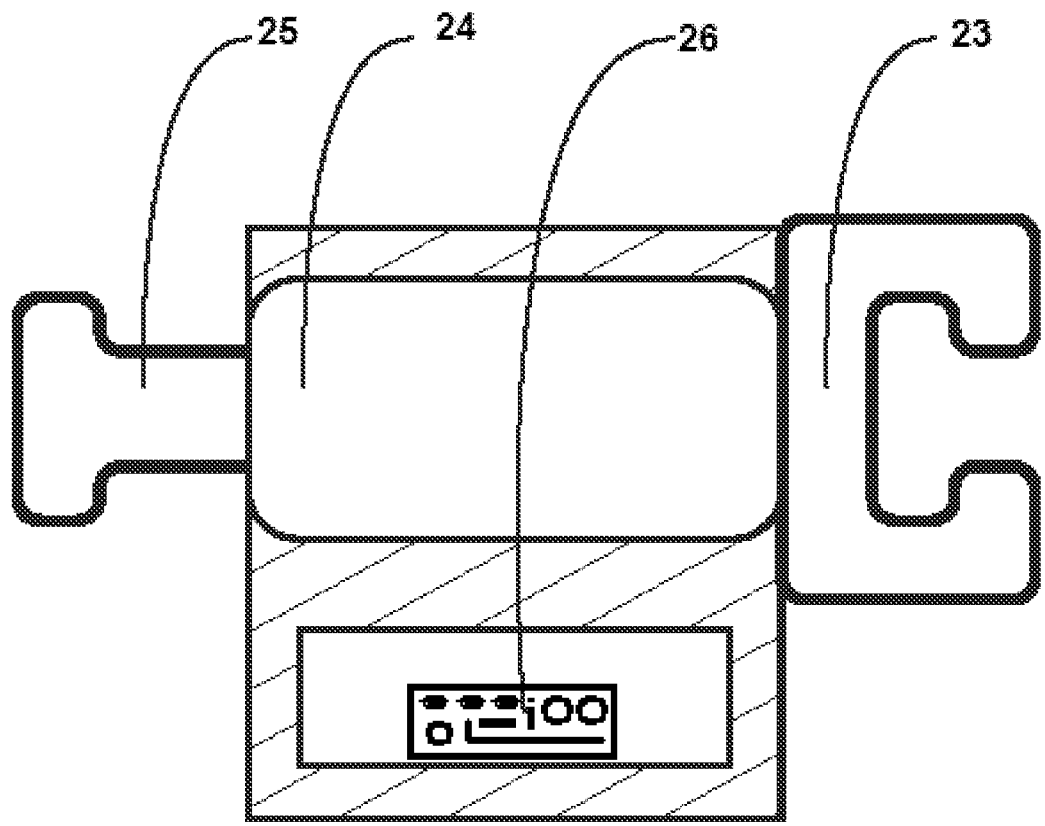
FIG. 4 illustrates a force sensing module in accordance with the invention.

Referring to FIG. 4, load cell 24 is disposed to be connected between patient applied parts 14 and traction application devices 16 using mechanical connections 23 and 25 respectively. Load cell 24 converts tension force into an electronic signal. This signal is directed to amplifying and transmitting circuitry 26 which serves to amplify the signals generated by load cell 24, convert the resulting analog signals to digital signals and transmit these signals over a wireless connection.

Figure 5:
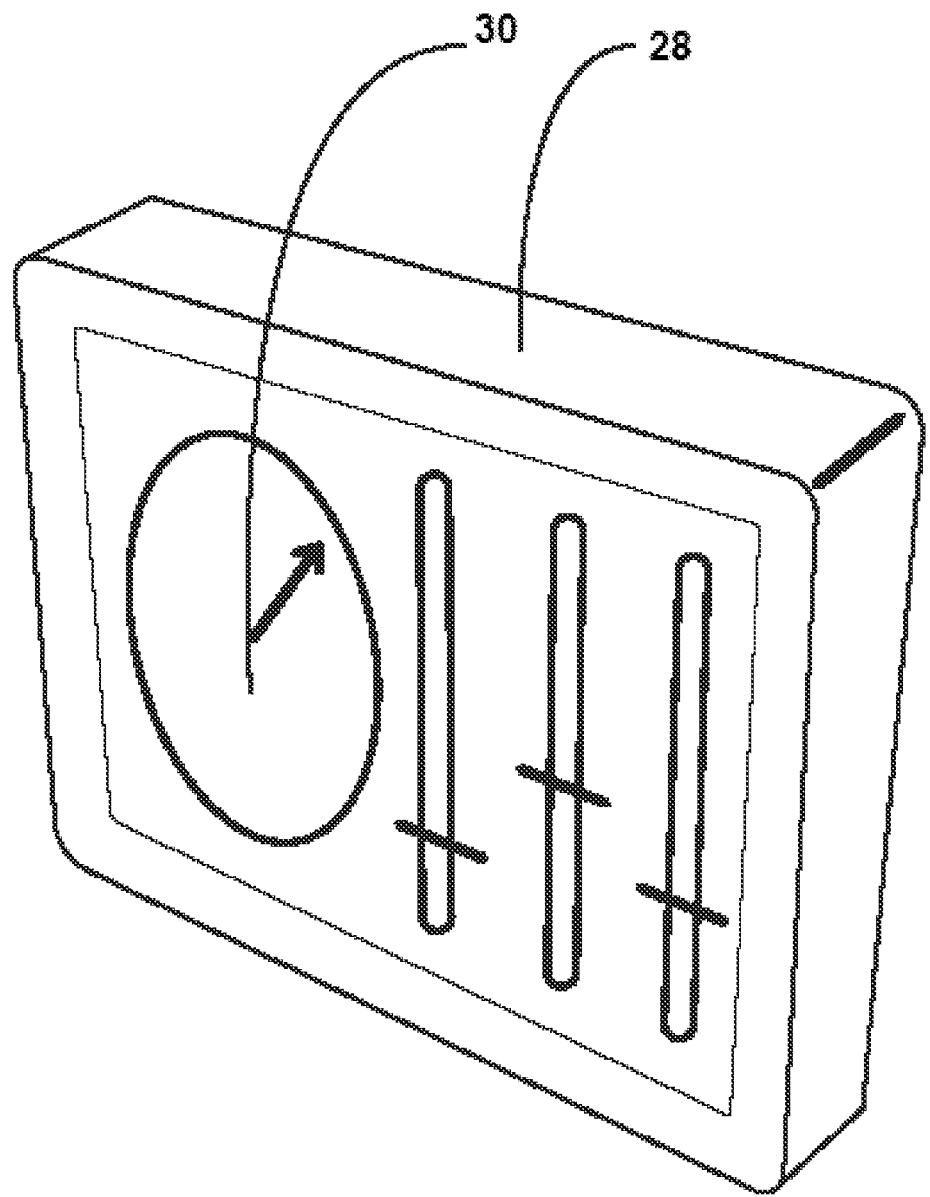
FIG. 5 depicts a computer touch screen for receiving and displaying force data in accordance with the invention.

FIG. 5 shows display device 28. Display device 28 incorporates a computing device, means for receiving the wireless signals from circuitry 22 and circuitry 26, enabling display device 28 to receive signals representative of the direction and magnitude of the force applied to perineal post 18, and to receive signals representative of the magnitude of the forces applied along the longitudinal axes of load cells 24.

Display device 28 incorporates a software program to analyse the signals representative of the forces applied to perineal post 18 and load cells 24, and display 30 to display the magnitude of the forces in graphical and numeric form. Further, the software program displays the direction of the force applied to perineal post 18 in the plane of operating table 10 and with respect to the mid-line of patient 10's body.

Figure 6:
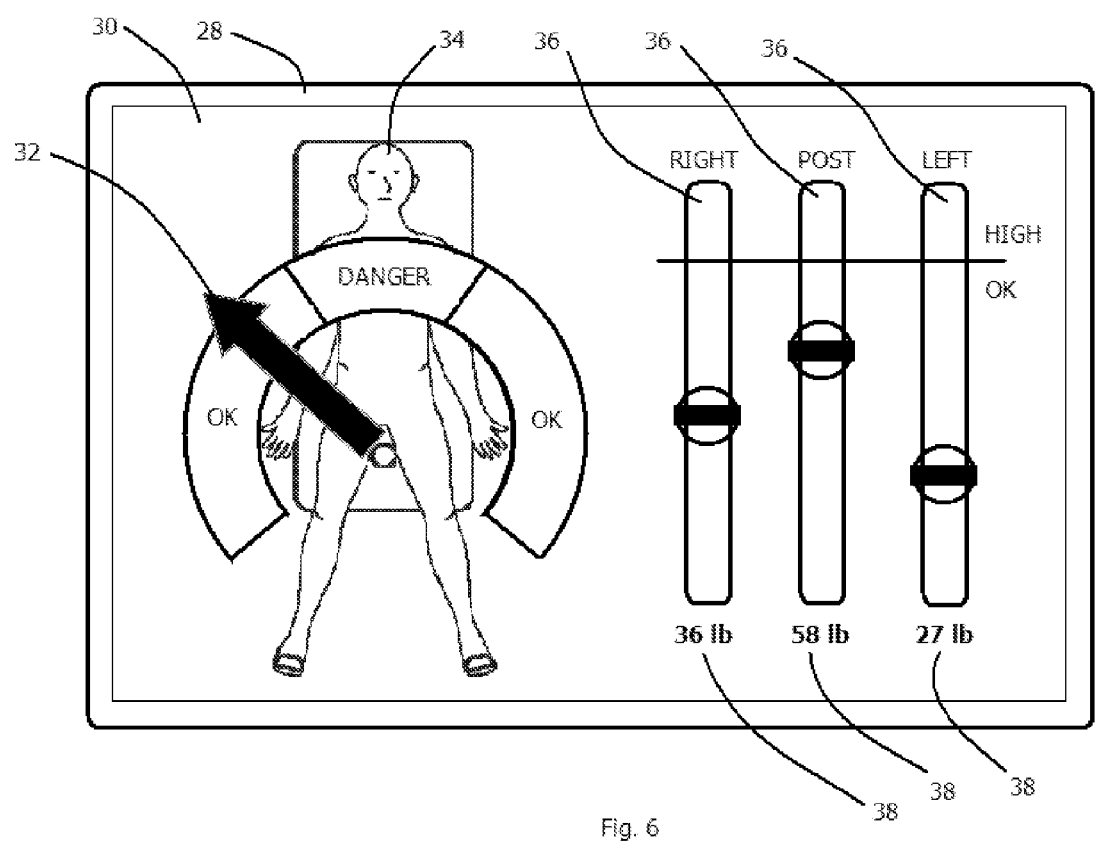
FIG. 6 illustrates a typical information display as it would appear on the computer touch screen of FIG. 5.

FIG. 6 shows a typical display as might be shown on display device 28. Force direction vector 32 on display 30 represents the magnitude and direction of the force applied by perineal post 18 to patient 10's body. Body outline 34 provides a reference for determining the direction of force direction vector 32 with respect to patient 10's mid-line. Indicators 36 display a graphical representation of the force applied to the right and left leg of patient 10 and the net force applied to perineal post 18. Numeric displays 38 show the numerical value of the forces applied to the right and left leg of patient 10 and the net force applied to perineal post 18.

In another aspect, the software program provides a means to provide visual and audible alarms should any of the forces detected by strain gages 20 attached to perineal post 18 or load cells 24 exceed pre-set limits.

In yet another aspect, display device 28 incorporates computer memory which is disposed to record the forces detected by strain gages 20 and load cells 24 at regular intervals so that a historical record of the forces and force vector applied to patient 10 may be kept.

In typical use, patient 10 is placed on operating table 12 in a supine position such that perineal post 18 is located in patient 10's groin. Load cells 24 are mechanically attached to traction application devices 16 and to patient applied parts 14. Patient 10's feet are placed into patient applied parts 14 and strapped into place with straps 15.

Display device 28 is placed in a location within view of the surgeon and turned on. Display device 28 receives signals from circuitry 22 and 26, analyses the signals to extract data representing the force measured by load cells 24 and strain gages 20, and displays this force data and the force vector determined by vector addition of the perpendicular forces measured by the two pairs of strain gages 20.

Vector addition as computed by the computer in display device 28 is done using simple and well-known formulas. If we define the signals from strain gages 20 as representing an X value and a Y value for the pairs of mutually perpendicular strain gages, where the Y direction is defined as the axis aligned with the mid-line of the patient's body, the formula for the magnitude of the vector addition of the two signals becomes:

$$F_{(result)} = \sqrt{(X^2 + Y^2)}$$

where $F_{(result)}$ is the magnitude of the vector sum of the two signals. Similarly, the formula for the direction of the vector addition of the two signals becomes:

$$\Theta_{(result)} = \text{Tan}^{-1}(X/Y)$$

where $\Theta_{(result)}$ represents the angle of the resulting net force vector with respect to the defined Y axis.

In preparation for the surgery, surgical staff now uses traction application devices to apply traction force to the operative and non-operative limbs of patient 10. While increasing the traction force, display device 28 is watched to monitor the forces applied to the limbs of patient 10, and to ensure that the resulting force vector applied to perineal post 18 does not approach the mid-line of patient 10.

During surgery, the surgeon can occasionally refer to display device 28 to ensure that movement of patient 10 during the surgery has not excessively increased the amount of traction applied to the limbs of patient 10, nor has resulted in force being applied directly along the mid-line of patient 10's body.

Many variations to the apparatus described herein may be constructed without departing from the scope and spirit of the present invention. For example, although the preferred embodiment uses four strain gages 20, similar results could be obtained using only two such strain gages, or by using other strain-measuring devices. Instead of using wireless connections as described in the preferred embodiment, a directly wired connection would provide a similar function.

While the present invention has been described in terms of a preferred embodiment, it will be appreciated by one of ordinary skill that the spirit and scope of the invention is not limited to those embodiments, but extend to the various modifications and equivalents as defined in the appended claims.

We claim:

1. A method for indicating forces applied to a patient's body while undergoing surgical traction, comprising the steps of:
    a) providing an operating table with a perineal post, said perineal post having plural strain gauges attached to said perineal post, said plural strain gauges connected to transmitting circuitry and configured for providing electrical signals proportional to a force applied thereto;
    b) locating a patient on the operating table with said perineal post located between said patient's legs;
    c) applying traction force to one or both of the patient's legs;
    d) with said strain gauges, measuring a force applied to said perineal post;
    e) calculating a direction of the force applied to said perineal post; and
    f) displaying the direction of the force applied to said perineal post.

2. The method according to claim 1 wherein step d) includes the step of measuring the force applied to said perineal post along two axes.

3. The method according to claim 2 wherein the two axes are generally perpendicular to one another.

4. The method according to claim 3 including the step of providing load cells to measure an amount of traction force applied to one or both of said patient's legs.

5. The method according to claim 4 including the steps of using a computing device to receive signals from said strain gauges and said load cells and with said computing device, analyzing said signals to generate data corresponding to a magnitude and direction of said traction force.

6. The method according to claim 5 including the step of displaying a force vector on a display associated with said computing device, said force vector representing the magnitude and direction of said force applied to said perineal post.

7. The method according to claim 6 including the step of displaying a graphical representation of the patient's body on said display and wherein the force vector is superimposed over a graphical representation of said patient's body.

8. The method according to claim 1 including the step of providing an alarm when the traction force applied to said perineal post exceeds a pre-determined limit.

9. The method according to claim 1 including the step of recording the traction force applied to one or both of the patient's legs.

10. A method for indicating forces applied to a patient's body while undergoing surgical traction, comprising the steps of:
    a) providing an operating table with a perineal post, said perineal post having plural strain gauges attached to said perineal post and capable of measuring forces applied to said perineal post along at least two different axes;
    b) locating a patient on the operating table with said perineal post located between said patient's legs;
    c) attaching a traction application device to both of the patient's legs and providing said traction application devices with a load cell for measuring tension applied to said patient's legs by said traction application devices;
    d) applying tension to one or both of the patient's legs with one or both of said traction application devices;
    e) with said strain gauges, measuring force applied to said perineal post;
    f) with said load cells, measuring the tension applied to one or both of the patient's legs; and
    g) calculating a direction of the force applied to said perineal post as tension is applied to one or both of the patient's legs and an amount of tension applied to one of both of said patient's legs.

11. The method according to claim 10 including the step of displaying on a display the direction and the amount of tension applied to one or both of the patient's legs with one or both of said traction application devices.

12. A method for indicating forces applied to a patient's body while undergoing surgical traction, comprising the steps of:
    a) providing an operating table with a perineal post, said perineal post having plural electrically conductive foil strain gauges attached to said perineal post;
    b) locating a patient on the operating table with said perineal post located between said patient's legs;
    c) applying traction force to one or both of the patient's legs;
    d) with said strain gauges, measuring a force applied to said perineal post;
    e) calculating a direction of the force applied to said perineal post; and
    f) displaying the direction of the force applied to said perineal post.

* * * * *